US005538752A

United States Patent [19]
Blanchette et al.

[11] Patent Number: 5,538,752
[45] Date of Patent: Jul. 23, 1996

[54] MELANIN COMPOSITIONS AND USES THEREOF AND RESULTING PRODUCTS

[75] Inventors: Robert A. Blanchette, Shoreview, Minn.; Theresa S. Brush, Burlington; Roberta L. Farrell, Groton, both of Mass.

[73] Assignees: Regents of the Univ. of Minnesota, Minneapolis, Minn.; Sandoz Ltd., E. Hanover, N.J.

[21] Appl. No.: 388,079

[22] Filed: Feb. 13, 1995

Related U.S. Application Data

[63] Continuation of Ser. No. 925,364, Aug. 4, 1992, abandoned.
[51] Int. Cl.$^6$ .............................. A01G 7/06; A01C 1/06; C09K 3/00
[52] U.S. Cl. .................... 427/4; 47/57.6; 106/15.05; 252/384; 424/78.03; 424/78.09; 424/78.36; 424/78.37; 427/160; 514/415
[58] Field of Search ................ 252/384; 435/117; 424/78.03, 59, 78.37, 78.36, 78.09; 514/415; 427/160, 4; 106/15.05; 47/57.6

[56] References Cited

U.S. PATENT DOCUMENTS

| | | | |
|---|---|---|---|
| 4,919,921 | 4/1990 | Hatae | 424/62 |
| 5,218,079 | 6/1993 | Pawelek et al. | 435/41 |
| 5,225,435 | 7/1993 | Pawelek et al. | 514/415 |
| 5,240,715 | 8/1993 | Ahene et al. | 424/574 |
| 5,256,403 | 10/1993 | Gaskin | 424/59 |

OTHER PUBLICATIONS

Cooke, et al., *Ecophysiology of Fungi*, "Resource Acquisition and Utilization," (1993) pp. 47–49).

*Primary Examiner*—Herbert J. Lilling
*Attorney, Agent, or Firm*—Robert S. Honor; Melvyn M. Kassenoff; Diane E. Furman

[57] ABSTRACT

Compositions comprising melanin or melanin precursors are useful for preventing or controlling decay of substrates such as cellulosic and other porous organic substrates. The compositions provide useful wood preservatives, wound dressings, and the like. In one embodiment, the compositions comprise melanin complexed with metal ions, particularly copper. The compositions may be applied as penetrating or surface treatments. Certain melanins are also particularly useful for removing metal ions from liquids.

33 Claims, No Drawings

MELANIN COMPOSITIONS AND USES THEREOF AND RESULTING PRODUCTS

This is a continuation of application Ser. No. 07/925,364, filed Aug. 4, 1992 and now abandoned.

FIELD OF THE INVENTION

The present invention concerns compositions based on melanin and their use in preventing or controlling decay of wood and other substrates to be protected against environmental factors. In another aspect, the compositions provide useful treatments of viable substrates such as tree wounds and seeds. Certain melanins are particularly useful in removing metal ions.

BACKGROUND OF THE INVENTION

Deterioration of timber and other substrates in the environment is a constant concern of the lumber and wood products industry and in agriculture. Infestation by brown rot fungi, for example, which attack at least the cellulose and hemicellulose of hardwoods or softwoods, is a major cause of decay, and has proved costly and difficult to control. Timber which is storaged or permanently exposed to the environment, such as construction materials, utility poles or railroad ties, must typically be impregnated or otherwise treated with fungicidal agents to obtain a useful life therefrom. Live substrates such as tree wounds if left unprotected also are vulnerable to invasive fungal decay, resulting in economic loss, particularly to the agricultural industry.

For preventing wood decay caused by fungal and other microbial agents, workers in the art have come to rely on the biocidal action of certain compounds of recognized toxicity in the environment, such as chlorinated hydrocarbons, inorganic and organic metal salts (e.g., arsenates, chromates, borates), and alkylaluminum compounds, representative ones of which comprise pentachlorophenol, copper chromium arsenate, acid copper chromate, chromated zinc chloride, copper naphthenate, and dodecyldimethylammonium chloride, see Nicholas et al., "Interaction of Preservatives with Wood," in *The Chemistry of Solid Wood*, ACS, 1984. Many of such compounds, moreover, are commonly formulated with petroleum-based and other organic solvent vehicles, which solvents in themselves are often considered environmental contaminants, and may be costly and hazardous to handle, besides being restricted from certain agricultural applications. The well-known creosote oils are also commonly derived from oil or coal tar fractions. Alternatively, the water-soluble compounds, such as inorganic metal salts, if not readily fixed within the substrate, tend to be leached by moisture to form toxic or corrosive residues in the environment. As a result, the selection of anti-microbial agents for preservation purposes is becoming increasingly circumscribed by environmental regulations.

It has been an object to identify more environmentally compatible materials and compositions which can be applied to a substrate to inhibit or control environmentally-induced deterioration or decay, and in particular, decay caused by microorganisms such as fungi.

It has been a further object to provide preservative compositions which can be employed in agricultural uses.

SUMMARY OF THE INVENTION

It has now been found that compositions which comprise melanin can be applied to a substrate to control or inhibit decay due to environmental factors. When applied to a substrate such as wood, the melanin compositions control or protect against decay, particularly as caused by microorganisms such as brown-rot fungi. It has been discovered that melanin can act as a barrier-type material which can prevent or retard the invasion and development of decay organisms, and in this respect can serve as an effective anti-microbial agent. The melanin composition may also contain other anti-microbial agents and it is a particular aspect of the invention to use metal ions or other agents which can chemically bind to the melanin and which inhibit or destroy microbial growth. Hence, the invention includes the use of both melanin and melanin combined with anti-microbial agents which can chemically bind to the melanin and contribute added anti-microbial effect, particularly metal-complexed forms of melanin.

The present invention therefore involves as one particular aspect thereof the method of protecting or preserving substrates subject to decay which comprises applying thereto an effective amount of a composition comprising melanin, and in particular, melanin bound to an anti-microbial agent.

In a particular embodiment of the invention, the melanin compositions are applied to living plant material subject to fungal attack, such as plant wounds and seeds.

Natural melanins from certain fungal and animal sources are particularly practical for taking up metal ions for preservative use, and additionally, for the removal of metal ions from various sources where such removal is desired, e.g., in effluent treatment. Compositions based on such melanins are also provided by the invention. The invention further contemplates the use of synthetic melanins, or melanin precursor materials which can be reacted in situ, i.e. on the substrate to be treated, to form melanin compounds.

The invention also provides new and useful articles or substrates of which at least a surface portion thereof which is subject to invasion and decay caused by native fungi is preserved against invasion and decay by having at least its susceptible surface coated or impregnated with a decay-inhibiting effective amount of a melanin composition in accord with the invention.

DETAILED DESCRIPTION OF THE INVENTION

Melanin is widespread in nature, and the melanin compounds of the invention may be obtained fairly inexpensively from certain natural sources, or can be synthesized. The melanin may be used according to the invention in various forms, ranging from virtually unprocessed melanized material to melanin which is substantially free of associated native material, or synthetic melanin. It is preferred that the natural melanin be treated to remove all or a portion of associated native material.

Melanin is considered to be essentially non-toxic to animals, non-corrosive and environmentally compatible.

Melanin also has the capacity to take up anti-microbial agents, including particularly metal ions. Complexes such as with metal ions, for example, $Cu^{2+}$, remain stable over a relatively broad pH range which overlaps pH values which generally exist in the natural environment, i.e. about pH 4–9 and typically about pH 4–7.

The invention therefore in one particular embodiment involves melanin in association with at least one metal ion which is physiologically toxic, and therefore has anti-microbial or anti-fungal activity, e.g., copper, boron, zinc, tin, aluminum and mixtures thereof.

The term melanin is an omnibus term that describes a large family of natural and synthetic pigments of diverse origin and chemical nature. In nature melanins are manufactured, for example, by many fungi in the Ascomycotina and Basidiomycotina, including white-rot fungi (e.g., Xylaria species such as *X. hypoxylon* and *X. perscaria;* Ustulina species, including *U. vulgaris*); as well as Hypoxylon, for example, *Hypoxylon atropunctatum,* Ganoderma species such as *Ganoderma applanatum,* and Armillaria species). Other natural sources of melanin comprise certain staining fungi (e.g., Ophiostoma, Aureobasidium species such as *Aureobasidium pullulans*), yeast such as Phaeococcomyces (e.g., *Phaeococcomyces catenatus*) as well as animal species (e.g., squid, octopus, etc.), and also include in many animals, the epidermis and wool or hair. Additionally, melanin can be produced by transformed microorganisms, see EP 363,792 (1990). Synthetic melanin can also be prepared by chemical or enzymatic means, and even by electrochemical or photochemical methods. A comprehensive review of the synthesis and properties of melanin is provided by Crippa et al., "Chemistry of Melanins," in *The Alkaloids,* ed. by A. Brossi, Vol. 36, Academic Press, Inc., 1989, pp. 253–323, which is hereby incorporated by reference; and see also, *Merck Index,* Eleventh Edition, 5692 (1989).

Melanins are generally classified according to three major types, depending on the identity of the precursor monomeric unit from which the melanin polymer is ultimately synthesized.

First, the "eumelanins", which generally comprise poly-5,6-indole quinones, are black or brown, insoluble, nitrogenous pigments. "DOPA melanin," for example, is produced by oxidative polymerization of 5,6-dihydroxyindoles derived enzymatically from tyrosine via the precursor, 3,4-dihydroxyphenylalanine ("DOPA"). Intermediate compounds in the synthesis of DOPA melanin may comprise dopamine (3,4-dihydroxyphenethylamine), semiquinone, dopaquinone, 5,6-dihydroxyindole, and indole-5,6-quinone. Certain fungi can also produce eumelanin from alternate nitrogen-containing sources such as γ-glutaminyl-3,4-dihydroxybenzene (GDHBB).

Second, "phaeomelanins" (polydihydrobenzothiazines) are sulfur-containing, alkali-soluble, yellow to red-brown pigments produced by oxidative polymerization of cysteinyl DOPA (or a mixture of DOPA and cysteinyl DOPA), via 1,4-benzothiazine intermediates.

Third, "allomelanins" (i.e. "other" melanins) are pigments generally associated with plants or fungi which are produced from nitrogen-free precursors such as catechol, or alternatively 1,8-dihydroxynaphthalene (DHN) as an immediate precursor via a pentaketide pathway, see Bell et al., Biosynthesis and Functions of Fungal Melanins, *Ann. Rev. Phytopathol.* 1986, 24:411–51.

Given the multiplicity of reactive sites present on the precursor monomeric units, the melanin products formed by oxidative polymerization or other reaction of these units comprise a variety of irregular heteropolymers containing groups selected from free carboxyl and phenolic, alcoholic, carbonyl and methoxyl groups. Furthermore, in nature, the melanins may be closely associated with linked peptides, as well as carbohydrate, aliphatic hydrocarbon and fatty acid moieties.

Therefore, a melanin polymer is generally characterized primarily by the identity of its precursor monomeric unit and by its spectroscopic properties, rather than by exact structure or chemical formula. A useful compendium of properties commonly associated with melanin compounds is provided by Gallas, U.S. Pat. No. 5,116,884 (1992), (see, e.g., col. 7, ll. 55–66), which is incorporated by reference. In particular, melanin in general has been characterized by the following properties:

1. a polymer of a monomeric melanin precursor;
2. a polymer whose monomeric precursors can polymerize via free-radical oxidative mechanism;
3. a polymer having broad band optical absorption;
4. a polymer with a stable free-radical;
5. a polymer with a highly conjugated pi electron system;
6. an amorphous, three-dimensional, heterogeneous polymer of varying molecular weight.

Melanins are generally completely solubilized by hot alkaline solution (e.g., 1 M KOH or 1 M NaOH at 50°–70° C.), and are insoluble at neutral pH in hot or cold water, cold HCl, or common organic solvents (e.g., acetone, chloroform, ethanol). Melanin generally begins to be precipitated from solutions at room temperature at about pH 9, generally appearing as dark brown or black flocculant precipitates, and is essentially completely precipitated from hot concentrated mineral acids (e.g. 6 M HCl).

Fungal melanins are believed to be synthesized in the cell walls or extracellular region, and may be stored in specialized hyphal or spore structures. Certain fungi, such as Ustulina, produce black lines or "pseudosclerotial plates" on cellulosic substrates. The process of forming pseudosclerotial plates is believed to involve proliferation of hyphae within a zone of the substrate, hyphal swelling, and release of melanin. This melanin, often referred to as "zonal barrier melanin" may be associated with viable or non-living fungal cells, and can be recovered from the cellulosic substrate itself, e.g., field wood, by harvesting the wood and subjecting it to recovery techniques as described herein.

To obtain or isolate melanin from laboratory fungal or yeast cultures, the fungal cultures may be grown up in a conventional manner on conventional culture media, e.g., yeast nitrogen phosphate dextrose (YNPD) agar, or malt agar, in liquid or on solid media. The cultures are maintained at a temperature and for a time sufficient to result in formation of melanized structures, which in many cases may be produced only at restricted times in the fungal growth and development cycle. Generally, cultures of basidiomycetes are maintained at about 25°–30° C. for about 20–30 days, at which time the appearance of darkened areas serves to indicate that melanin is being manufactured. Yeasts or stain fungi will exhibit such darkened areas at about 2–15 days at 25°–35° C.

The black or otherwise pigmented areas of the fungal culture can be physically separated and recovered from the culture, and then subjected to various purification procedures, e.g., extraction into alkali, hydrolysis in acid, as described herein.

Particularly preferred melanins are obtained from animal sources including human hair and wool such as obtained from sheep (Ovis genus/Bovidae family) and other domestic animals which are wool producers or sources such as llamas, guanaco and related wool producing members of the camel family. Pigmented hair of animal species, particularly wool animals, is desirable because it is a relatively inexpensive source which may even be applied to a substrate in essentially unpurified form. Animal hair, particularly wool, is desirable because it has been found to complex high amounts of metal ions useful to enhance inhibition of microbial invasion, and prevent decay of susceptible substrates. Compositions comprising pulverized melanized wool will often advantageously contain secreted lanolin, which is a relatively adhering material which is a useful excipient in wound dressings and other topical applications, and is considered an agriculturally acceptable carrier. Animal hair, e.g., wool, after freezing with or in liquid nitrogen, may be essentially pulverized by immediate application of shearing forces, e.g., by using a simple mortar and pestle, or by grinding in a Wiley mill. Alternatively, the melanin particles can be chemically isolated from the hair or wool, as described below.

Melanin in nature is typically in a granular form, and is often associated with proteins, lipids and other cellular components. The usual method of preparing soluble melanin is to extract it into cold or hot alkali, precipitate it with acid, and hydrolyze proteins, carbohydrates, and lipids away from it by prolonged refluxing in aqueous acid, e.g., 6 N HCl, Bell & Wheeler at p. 428. Acid treatment for 7 to 14 days is usually effective to reduce the protein content to not more than 5% by weight of the melanin, more usually not more than 1% by weight. The melanin can be further purified away from lipids and the like by washing with an organic solvent, e.g., ethanol, ether or tetrahydrofuran, to remove lipid or wax-like materials, optionally alternated with additional hydrolysis in hot acid. The purified melanin residue which is recovered can then be dried and/or suspended or dissolved or otherwise combined with an appropriate medium.

In general, aqueous preparations of melanin may be prepared by solubilizing the melanin in hot (i.e. 50°–70° C.) alkaline solution having a pH of about 10 and above, such as 1 N ammonia, sodium hydroxide or potassium hydroxide solution. The solution may then be cooled to room temperature without substantial precipitation of the melanin.

Aqueous suspensions may be prepared either by bringing down the pH of an alkaline solution of the melanin to about 9, or by simply adding melanin to an aqueous medium at pH 4 to 9, and preferably 5 to 7, and preferably blending.

Synthetic melanins can be prepared by means known to the art, via enzymatic and/or chemical oxidative polymerization of a melanin precursor compound. For the purposes hereof, melanin precursors are monomers and dimers and the like (intermediates) which upon polymerization or condensation or other reaction form polymeric substances having the properties of melanin.

Eumelanins and phaeomelanins are typically synthesized by reacting a precursor in the presence of commercially available mushroom tyrosinase. DOPA, dopamine, or tyrosine are generally utilized as substrates in the preparation of synthetic eumelanins. For example, DOPA melanin can be prepared by known means by reacting D,L-DOPA or L-DOPA with tyrosinase in pH 6–7 buffer in air for two weeks; the reaction can be accelerated by bubbling air through the mixture, raising the temperature up to about 38° C., or adding a chemical oxidizing agent, such as ammonium persulfate, ferric chloride, or magnesium perchlorate.

Melanins can also be formed by autooxidation of a suitable precursor. For example, melanin derived from DOPA, catechol or DHN precursors can typically be prepared by bubbling air or oxygen through an aqueous solution of DOPA or catechol brought to pH of about 8 or above with, e.g., ammonium hydroxide, concentrated ammonium, sodium hydroxide, or the like.

The polymerization reaction may also be initiated in solvents other than water using a free-radical initiator selected from peroxides, azo compounds, redox pairs, photochemical systems, perborates, percarbonate, and radiation. Suitable organic solvents such as DMSO, chloroform, toluene and 1,2-dichloroethane, may also be utilized as a reaction medium.

Synthetic phaeomelanin can be obtained by oxidizing L-tyrosine or L-dopa in the presence of excess cysteine at pH of about 6–7.

The resulting melanin is collected by filtration, fractional sedimentation or centrifugation, and preferably these steps are preceded by acidification of the reaction medium to pH 3.5 or below.

In the practice of the invention, synthetic melanins can also be prepared "in situ" from precursor compounds, i.e. the melanin is synthesized on the substrate by applying to the substrate a composition comprising the melanin precursor under conditions which facilitate the formation of melanin. For example, catechol or 1,8-dihydroxynaphthalene (DHN) once applied to a substrate may simply react in air at slightly alkaline pH to form melanin, particularly if metal ions are present. Alternatively, the melanin precursor may be combined with the enzyme or free-radical initiator on the substrate under conditions which facilitate formation of melanin.

Therefore, the term "melanin" as used herein shall be understood to include the synthetic melanin substances formed from melanin precursor compounds.

Such reaction may simply result from exposure to air at ambient temperature, or the melanin precursor may be applied together with an appropriate initiator compound or enzyme and solvent which facilitate polymerization of the precursor to form melanin.

Suitable precursor compounds include D,L-DOPA, D-DOPA, L-DOPA; tyrosine, 5,6-dihydroxyindole, catechol,1,8-dihydroxynaphthalene, 5,6-dihydroxyindole-2-carboxylic acid, tyramine, 3-hydroxytyramine (dopamine), tyrosine, 5-hydroxyindole, leucodopachrome, tryptamine, serotonin (with enzyme), epinephrine, norepinephrine, adenochromedopamine, m-aminophenol, o-aminophenol, p-aminophenol, 4-aminocatechol, 4-methylcatechol, 2-hydroxy-1,4-naphthaquinone, 3,4-dihydroxybenzylamine, 3,4-dihydroxybenzoic acid, 1,2-dihydroxynaphthalene, gallic acid, resorcinol, 4,5-dihydroxynaphthalene-2,7-disulfonic acid, p-aminophenol, and mixtures thereof.

Of these, D,L-DOPA, D-DOPA, L-DOPA, tyrosine, dopamine, 5,6-dihydroxyindole, catechol, and 1,8-dihydroxynaphthalene are preferred. D,L-DOPA, L-DOPA and catechol are more preferred, and L-DOPA and catechol are even more preferred. Catechol, in particular, is a naturally available inexpensive starting material which can be readily utilized.

Natural or synthetic melanin or melanin precursors or intermediate compounds can be obtained commercially or can be prepared from known starting materials using methods known to the art.

In a further embodiment of the invention, the melanin or melanin precursor is combined with at least one metal ion. When melanin is contacted with a source of metal ions, various types of binding have been postulated to occur. For example, carboxyl or phenolic groups of the melanin will generally participate in ion-exchange type reactions by binding with metal ions and releasing hydrogen ions. Oxygen-containing groups of the melanin, including phenolic and alcoholic hydroxyl, carbonyl and methoxyl groups, as well as amine groups, may also be involved in bonding to form metal-organic complexes possibly in the form of chelates, Gadd et al., Biosorption of copper by fungal melanin, *Appl. Microbiol. Biotechnol.* (1988) 29:610–617; see also, Iron and Copper Binding by Fungal Phenolic Polymers: an Electron Spin Resonance Study, *Current Microbiology* 10: 281–285 (1984). Metals which to varying degrees are toxic to fungi, when complexed to the melanin, are useful to increase fungicidal effectiveness. Advantageously, said metal-complexed melanin compositions can be diluted by water to form suspensions, and once applied to a substrate may remain stable (i.e. without leaching metals) over prolonged periods of time.

Suitable metal ions in the compositions of the invention include metals such as copper, manganese, boron, tin, aluminum, zinc, nickel, cobalt and cadium, as well as calcium, magnesium and sodium, and mixtures of the foregoing. Preferred among such metals are copper, boron, zinc, tin, aluminum, and mixtures thereof, most preferably copper.

Suitable sources of metal ions comprise water-soluble compounds, e.g., metal salts, such as sulfates, carbonates, acetates, etc. Sulfate compounds are preferred.

It has been found, in particular, that animal melanin, particularly wool melanin, binds metal ions very effectively, making compositions comprising sheep wool among the preferred compositions of the invention. Wool, e.g., sheep's wool, will bind copper at copper concentrations at least as high as about 125,000 milligram of copper per kilogram of the total composition. Compositions comprising wool melanin complexed with ions of at least one physiologically toxic metal in amount of at least 5% by weight of ion based on the metal, preferably at least 10%, more preferably at least 12.5%, are particularly useful compositions in accord with the invention.

In order to form a complex of melanin or melanized biomass with a metal, an aqueous suspension is prepared comprising the melanin and the source of metal ion. The suspension is preferably maintained at about pH 5–7.

The rate of adsorption of metals on the melanin can be affected by metal concentration, pH of the medium, and amount of melanin present. The source of metal ion may be provided to the suspension within a broad range of concentrations at which such compound remains dissolved. Melanin concentration may also be within a broad range over which the melanin can be maintained in suspension. The medium is maintained for a time sufficient to result in complexation of the metal ions with the melanin, which can range from minutes to hours. As the melanin takes up the metal, the resulting complex generally remains in suspension. The concomitant release of $H^+$ ions into the medium can result in a slight lowering of the pH. The pH should in any case not be permitted to fall below a point at which metal ions would be desorbed from the melanin. It is generally satisfactory to maintain pH of the aqueous medium comprising melanin complexed with a metal within the range of about 4 to 9, and preferably about 5 to 7. The resulting suspension of complexed material, once separated from any excess metal salts, can therefor be used directly in the invention, or the melanin-metal complex can be isolated and/or combined with another vehicle, e.g., carrier.

Compositions containing melanin for use in accord with the invention may be formulated in widely varying ways to obtain the benefits of melanin in preserving substrates to which the compositions are applied. It is considered a part of the invention to use melanin either as a relatively minor or principal contributing component in the compositions and the protective coatings or barriers which they will form. Hence, melanin may be combined in the compositions with a wide variety of other substances which desirably do not increase the susceptibility of the substrate to invasion or decay. Preferably, other substances such as pigments and polymeric materials which will contribute to preservative properties of the composition and inhibit invasion or decay by environmental factors, particularly microorganisms, will be used. In addition to anti-microbial agents which can be chemically bound to melanin and remain in active, chemically-bound form with the melanin, the compositions may include any of a host of anti-microbial agents which do not chemically bind, particularly fungicides, to enhance the effectiveness of the compositions. Similarly, preservative compositions for particular purposes such as seed coatings or dressings may include such additives as plant nutrients. In a like manner, compositions for use in wound healing may include ingredient conventionally useful in such compositions, such as lanolin.

In addition, while it is preferred to use a highly purified melanin, it has been found that crude melanins containing components associated with melanin in nature, for example, as obtained from fungi or animal hair, including particularly proteinaceous substances, may be effectively used and thereby reduce the costs of such compositions.

Coatings and similar surface treatments formed on substrates to inhibit invasion or decay in accord with the invention may therefore contain as little as 5% by weight melanin, but preferably contain at least 15% by weight melanin and more preferably at least 25%. The still more preferred coatings contain 30% to 100% by weight melanin, more usually 30% to 80% melanin.

Dilute liquid compositions for forming the protective coatings of the invention may generally comprise as little as 2% by weight melanin based on the overall composition which includes the liquid vehicle for carrying and forming the protective coatings of the inventions. Preferably, such application compositions contain at least 6% by total weight of melanin and more preferably at least 10% by weight melanin. The still more preferred compositions contain 12% to 80% by weight melanin, more usually 12% to 60% by weight melanin. Water is the generally suitable and preferred liquid vehicle or carrier for the melanin in such compositions, although other liquids which suspend or dissolve the solid coating components may be used. The compositions for applying the coatings of the inventions may include a host of other materials of a protective nature, as indicated above, and, in addition, other agents to facilitate coating and/or the stability of the application compositions. Aqueous compositions, for example, may contain agents to balance or buffer the compositions at desired pH levels, and other agents such as wetting agents. In general, such compositions may be in any of several forms including suspensions, solutions, emulsions, pastes slurries and the like. Compositions for particular purposes such as wound dressings, seed coatings and other agricultural purposes will employ an agriculturally acceptable carrier, preferably water. For seed coatings or dressings, the melanin and its compositions may be employed in dust or granular form to form a suitable coating, as well as in liquid form. While melanin seed coatings can contain complexed metals, reduced amounts thereof or melanin without added metal ions may be employed and one may take advantage of the ability of melanin to take up metal ions from the soil to provide enhanced seed protection and closer proximity of metal ion nutrients to the seed. Melanin compositions in general provide very good seed coating and will protect the seed against a host of undesirable soil borne fungi such as Fusarium, Pythium, Rhizoctonia, Pseudocercosporella and the like.

Compositions may also be prepared comprising the melanin pigment or precursor incorporated within or adsorbed onto polymeric particles or beads. Alternatively, melanin-containing films can be formed on a substrate by applying to the substrate a solvent solution of the melanin or melanin precursor and a film-forming polymer, optionally in combination with various suitable catalysts, stabilizers, wetting agents, etc., which is then preferably cured. Suitable polymers are of a diverse nature, including celluloses, (meth)acrylates, polyamides, polyacrylates, and other conventional natural or synthetic polymers.

The melanin compositions may be applied to any of a wide variety of substrates which are susceptible or subject to decay caused by environmental factors, particularly microbial action. Such substrates involve inanimate objects of all sorts including structural materials or components including particularly those susceptible to brown rot fungi, particularly those containing cellulose such as tree wood, e.g., lumber, railroad ties, utility poles and the like. Other cellulose-containing or fiber-based articles which may be mentioned for treatment include textiles, cordage and the like. Animate objects which may be treated are those from the plant kingdom and specific applications of interest particularly include wound healing and seed coatings or dressings.

Application of the compositions to a substrate may be by any of the methods well-known to those skilled in the art including penetrating and topical treatments, for example, long or short steeping, spraying, or methods involving application of vacuum and/or pressure or simple contact of the solution with the surface of the material to be treated. Dusts and other dry forms, e.g., granular forms, may be used in seed coatings or dressings.

For plant wound treatment, the melanin is indicated to function as a barrier material that seals the exposed xylem and prevents entrance of microorganisms. It has been found that while, for example, a fatty material such as lanolin alone is somewhat effective as a barrier against fungal infestation, a composition comprising both melanin and a viscous material such as lanolin can provide improved wound closure and enhanced resistance against fungal colonization and wood discoloration by fungi. When applied to plant substrates, the compositions of the invention may be employed at any time during the growing season or during a dormant period. The wound treatments are preferably applied as soon as possible after wounding for best results in establishing an effective barrier.

Melanins generally may be used to remove metal ions from liquids including aqueous waste streams in which metal ions are undesirable. It has been found that certain melanins are particularly useful and efficient in removing high amounts of ions from such liquids and the invention also provides for the use of such melanins in removing such ions from liquid. Such particularly useful melanins include animal melanins, particularly wool melanins including sheep melanin, and also melanin from black pigmented fungi of the genuses Xylaria, Ustulena and Phaeococcomyces, for example, the species thereof identified herein. Wool melanin is generally preferred. Such removal may be readily accomplished using melanin either in aqueous medium or in dry form. Preferably, the melanin, in dry form, is used as packing in a vertical column or tower and the liquid to be treated is filtered down through the melanin packing to effect a substantial reduction or essential removal of metal ions from the liquid, e.g., from aqueous metal ion-containing waste streams. Such process may be conveniently carried out at ambient temperatures and in the presence or absence of pressure to facilitate movement of the liquid through the column. The melanin, when saturated with recovered metal ions, may be discarded but the saturated melanin may also be treated in an ion-exchange reaction with, for example, with 0.5–1.0 M HCl or EDTA (ethylenediamine-tetracetic acid) to recover the removed metal ions and the thus treated melanin may be reused. It is also advantageous that the melanin may be used in purified or in crude form in removing metal ions.

The following Examples are provided for purposes of illustration only.

EXAMPLE A

Isolation and Purification of *Xylaria melanin*

(a) Sterile 1 liter tissue culture bottles containing 50 ml. of a solid agar medium comprising 2% agar, 2% malt extract and 0–0.2% yeast extract were inoculated aseptically with mycelial fragments of the ascomycetes *Xylaria hypoxylon* and *Xylaria perscaria*. The bottles were loosely capped and were maintained at 25° C. for 3 months. The *X. perscaria* culture developed long black stalks with white tips. The *X. hypoxylon* grew less rapidly and exhibited short knobby stalks. After three months, the mycelial mats and stalks were harvested from the agar surface. Residual agar which adhered to the harvested mats was melted in a microwave oven and poured off.

(b) The mycelial mats and stalks were blended in a Waring blender at high speed for approximately 1–2 minutes while adding 100 ml. of water. The resulting material was mixed with an equal volume of 12 M HCl to form a slurry. 500 ml. of the slurry was refluxed for 22 hours in a 1-liter round bottom flask equipped with a reflux condenser. The mixture was allowed to cool overnight to allow undissolved solids to settle.

The dark brown supernatant was decanted, and the remaining solids were refluxed in 500 ml. of 6 M HCl for 24 hours. The solids were recovered and the acid treatment was repeated.

(c) The recovered solids were again combined with 500 ml. of 6 M HCl, and the flask was set aside at room temperature for 1 week.

(d) The resulting mixture was centrifuged at 6,000 rpms for 20 minutes. A black material was collected which was water washed to neutral pH and then refluxed in 95% ethanol overnight to remove fungal lipids.

(e) The material was again centrifuged at 6,000 rpms for 20 minutes, water washed and lyophilized to dryness.

EXAMPLE B

Isolation and Purification of *Ustulina vulgaris* melanin

Sterile 1 liter tissue culture bottles containing 50 ml. of an aqueous growth medium comprising 1% soytone and 4% glucose were inoculated aseptically with black mycelia of *Ustulina vulgaris*. The cultures were maintained at 25° C. for 3 months, during which time the white fungal mats gradually turned black.

The black mycelial mats were collected from the liquid cultures and the procedure of Example A, steps (b)–(e), was followed, except that in step (c) the solids combined with fresh 6 M HCl every 24 hours for the first 3 days, then every 48 hours for the remainder of the week.

A black granular material was collected.

EXAMPLE C

Extraction of *Ustulina vulgaris* "zonal barrier" melanin from field collected wood "Zonal barrier" melanin present in pseudosclerotial plates of *U. vulgaris* was isolated from field wood as follows:

(a) 41.7 g. of oven dried wood pieces were extracted four times with 800 ml. of 0.5 M NaOH at 75° C. for 4 hours each time. The brown liquid collected after each extraction was filtered through glass wool to remove any particles of wood. The filtrates were adjusted to pH 1.5 with 6 M HCl. The brownish black precipitate which settled out was collected by centrifugation at 6,000 rpms for 20 minutes. The solids from each extraction were combined and washed with distilled, deionized water to remove residual alkali.

(b) The solids were hydrolyzed by refluxing in aqueous 6 M HCl over 24 hours. The solids were recovered and the hydrolysis was repeated.

(c) The undissolved solids were collected by centrifugation at 6,000 rpms for 20 minutes, and water washed to neutral pH. The resulting dark brown material was lyophilized to dryness.

EXAMPLE D

Extraction of melanin from *Phaeococcomyces catenatus*

*Phaeococcomyces catenatus*, a black yeast, was grown in shake flasks on Sabourand's Dextrose Broth (30 g/l), pH 7.0, or on 2% malt extract/0.2% yeast extract, at 25° C., 200 rpms.

The biomass was harvested by centrifugation at 10,000 rpms for 15 minutes. The cells were washed several times with distilled water and lyophilized.

EXAMPLE E

Extraction of Melanin from Black Sheep Wool and Complexation with Metal Ions Wool of black sheep was washed with soap and water to remove foreign matter and air dried. 50 g. of wool in 500 ml. of 0.5 M NaOH was maintained at 70° C. for 4 hours. The solution was cooled, filtered through glass wool, and 6 M HCl added to lower the pH to 3.3. A precipitate settled out over night and was collected by centrifugation at 8,000 rpms for 20 minutes, washed several times with distilled, deionized water and lyophilized.

Dried wool melanin, 4 grams, was added to 200 ml of 50 mM $CuSO_4$ or $ZnSO_4$, the pH adjusted to 6.0, and the suspension stirred overnight at 23° C. The melanin was collected by centrifugation, washed 4 times with distilled, deionized water, and lyophilized.

EXAMPLE F

Synthesis of DOPA Melanin (1) Enzymatic synthesis

Following the general procedure described by Ito, S., *Biochimica et Biophysica Acta* 883 (1986) 155–161, 2 mg. of mushroom tyrosinase (Sigma) (2,200 Unit/mg, polyphenol oxidase activity) were combined with 1 mmole of L-3,4-dihydroxyphenylalanine (L-DOPA) in 80 ml. of (a) 50 mM sodium carbonate, pH 9.5 or (b) 50 mM sodium phosphate, pH 6.5. The reaction mixtures were incubated overnight at 37° C. in a shaking water bath.

The pH was adjusted to 1.5 with aqueous 6 M HCl, and black solids precipitated in each reaction medium. The solids were collected by centrifugation at 6,000 rpms for 20 minutes, washed with distilled, deionized water, and lyophilized.

(2) Chemical synthesis (i) DOPA melanin. Following a procedure adapted from Froncisz et al., *Arch. Biochem. Biophys.* 202,289 (1980), 15 g. of DL-DOPA (Sigma) were dissolved in 3 liters of water (Milli-Q Plus). The pH of the resulting reaction medium was adjusted to 8.0 with concentrated ammonium hydroxide. Air was bubbled through the medium, which was maintained for 5 days at a temperature of 45° C. The pH was re-adjusted to 8 each day. The solution turned black within a few hours of heating.

The medium was acidifed to pH 1.55 with 6 N HCl, and centrifuged at 8,000 rpm for 10 minutes. The melanin solids were collected and washed four times with 10 mM HCl and three times with deionized water, and lyophilized.

(ii) Catechol melanin was prepared by the same procedure as above.

EXAMPLE G

In Situ Synthesis of Melanin from Precursors

A. DOPA Melanin

Ten grams of D,L-dihydroxyphenylalanine (D,L-DOPA) (Sigma) were added to a 200-ml beaker containing one liter of water (Milli-Q Plus) with mixing, to form a clear aqueous medium. Aspen blocks, each 15 mm×15 mm×8 mm, were placed in the beaker and kept submerged by plastic discs placed over the blocks. Immediately after addition of the blocks, the pH of the medium was 4.2.

The contents of the beaker were stirred for 24 hours, and then the pH was adjusted to 8.0–8.5 with concentrated ammonium hydroxide. The aqueous medium was observed to gradually darken over time. Stirring was continued for another 24 hours.

The wood blocks were recovered from the aqueous medium and vacuum dried. It was observed that the black color had completely penetrated throughout the block.

B. Catechol Melanin

In the same manner as above, aspen wood blocks were treated with an aqueous 10% solution of catechol.

After adjusting the pH to 8.0–8.5, the solution and wood blocks were observed to be golden brown in color.

C. Control

Aspen wood blocks were treated in the same manner as in A. above, except that no melanin precursor compound was added to the aqueous medium. The medium remained clear and the blocks did not darken or otherwise change coloration.

General Procedure

In the procedure of the following examples, melanin formulations were prepared in three concentrations in water (5 mg/ml, 50 mg/ml, and 100 mg/ml) from stock solutions diluted with phosphate buffered saline. The stock solutions were prepared by first solubilizing the melanin in 1 ml. of 0.5 M NaOH at 60° C. for 2 hours, then cooling the solution to room temperature. The pH was brought down to about 5–5.5 with aqueous 1.0 M HCl, and the volume of solution was adjusted to 5 ml. with phosphate buffered saline. Dilutions were then prepared from these stock solutions. Control samples, i.e. without melanin, comprised 0.5 M or 1.0 M NaOH solution brought to pH 5.5 with 1.0 M HCl. The volume was adjusted to 5.0 ml. with phosphate buffered saline.

Birch wood blocks (hereinafter in the aggregate, "Block A"), 7.5 mm on each side, were dried at 75° C. for 48 hours. The dry weight of each block was recorded. The blocks were submerged for 15 minutes (Example 1) or 12 hours (Examples 2–6) in the above-prepared melanin compositions and the control. (In Example 4, the bottle was shaken in a rotary shaker during this time.)

The blocks were removed to wax paper and allowed to dry at room temperature for 1–2 hours, and in an oven at 75° C. for 48 hours. The weight of each block was taken.

In Example 1, each treated block "A" was placed on top of a larger oven-dried, weighed birch block (hereinafter in the aggregate, Block "B") which was not pre-treated with a melanin composition. In Examples 2 to 6, only treated Blocks "A" were employed. The blocks were placed in a bottle containing 10 ml. of vermiculite and 7 ml. of water, and autoclaved for 30 minutes at 121° C.

The blocks were then inoculated with the brown-rot fungus, *Fomitopsis pinicola*, by aseptically applying to the top surface of Block "A" mycelial mats obtained from cultures of the fungi.

The bottle was stored for 12 weeks in a humidity/temperature controlled chamber at about 90% humidity and 27° C., after which time the blocks were removed from the bottles, any adhering vermiculite or fungus was lightly brushed off the surface, and the blocks were oven dried and weighed.

The percent weight loss of melanin-treated Block A (and in Example 1, untreated Block B) was determined and are provided in the following Tables. The weight loss provides an indication of the extent to which fungus has been able to attack the wood: the greater the weight loss, the more extensive the fungal attack, and conversely.

EXAMPLE 1

The General Procedure was followed employing Ustulina melanin obtained as in Example B.

TABLE 1A

| Inhibition of Decay Fungi in Treated Block "A". | |
|---|---|
| Melanin Concentration (mg/ml) | Fungal Melanin *F. pinicola* Percent weight loss of wood block |
| CONTROL | 10.4 ± 8.1 |
| 5 | 7.3 ± 4.9 |
| 50 | ND |
| 100 | −13.9 ± 5.8* |

*no weight loss
ND - not determined

In all cases, the Blocks "B" showed a weight similar to blocks which had not been treated with melanin.

EXAMPLE 2

The General Procedure was followed employing zonal barrier *U. vulgaris* melanin obtained as in Example C.

TABLE 2

| Inhibition of Decay Fungi by *U. vulgaris* Zonal Melanin. | |
|---|---|
| Melanin Concentration (mg/ml.) | *F. pinicola* Percent weight loss of wood block |
| CONTROL | 56.2 ± 6.7 |
| 10 | 8.3 ± 3.4 |
| 50 | — |
| 100 | 8.7 ± 0.5 |

EXAMPLE 3

The General Procedure was followed employing *X. perscaria* melanin obtained as described in Example A.

TABLE 3

| Inhibition of Decay Fungi By *X. perscaria* melanin. | |
|---|---|
| Melanin Concentration (mg/ml.) | *F. pinicola* |
| CONTROL | 66.6 ± 0.5 |
| 10 | 63.4 ± 1.2 |
| 50 | 7.9 ± 0.6 |
| 100 | 9.5 ± 1.5 |

EXAMPLE 4

Formation of Melanin-Metal Complexes (A) Complexation with Zinc or Copper

Copper or zinc were complexed to melanin obtained from black sheep wool (as described in Example E) or *P. catenatus* (as described in Example D).

(1) 4 g. dry weight of each of the above melanins were added to 200 ml. of 50 mM copper sulfate or zinc sulfate solution to form a suspension. The pH was adjusted to 6.0 with 1 M NaOH and the suspension was stirred overnight at 23° C.

(2) The metal-complexed melanin solids were recovered from by centrifugation at 6,000 rpms, washing with distilled, deionized water and lyophilization. The resulting solids were resuspended in phosphate buffered saline at pH 7–7.5 to a concentration of 50 mg/ml and applied to birchwood blocks by the General Procedure described above, with the results provided on the following table.

A control sample comprised 50 mg/ml suspensions of melanin obtained from the above-indicated sources which were not complexed with metals.

TABLE 4A

Inhibition of Decay Fungi by Sheep Wool and *P. Catenatus* Melanin and Metal Complexes Thereof

| Melanin | Percent Weight Loss of Wood Block | |
|---|---|---|
| | *F. pinicola* | No fungus |
| Wool + $Zn^{2+}$ | 4.44 ± 0.89 | |
| Wool + $Cu^{2+}$ | 5.30 ± 1.8 | |
| *P. catenatus* + $Zn^{2+}$ | 4.98 ± 3.53 | |
| *P. catenatus* + $Cu^{2+}$ | 6.79 ± 0.42 | |
| Control (no metal) | 24.65 ± 12.81 | 0.97 ± 0.64 |

B. Complexation with Copper or Boron

Copper or boron were complexed to melanin obtained from: (1) *U. vulgaris*, (2) *X. perscaria*, (3) *U. vulgaris* zonal barrier melanin, and (4) *P. catenatus*.

(1) Aqueous suspensions were prepared comprising one gram dry weight of each of the above melanins in 200 ml. of 5 mM copper sulfate solution, except the *P. catenatus* was suspended in 10 mm $CuSO_4$. The pH dropped to about 5.5 after 3 days and was readjusted to 6.

(2) Aqueous suspensions were prepared comprising one gram dry weight of each of the above melanins in 100 mM sodium borate solution, pH 7.0. The mixtures were stirred for 7 days.

(3) The solids were collected and resuspended by the procedure of step (2) of Part (A) above, and the General Procedure was followed, the results being provided on the following tables.

A control sample comprised 50 mg/ml suspensions of melanin obtained from the above-indicated sources which were not complexed with metals.

TABLE 4B-1

Inhibition of Decay Fungi by Melanin Control Sample

| | No Melanin Treatment | Melanin Source | | | |
|---|---|---|---|---|---|
| | | *P. catenatus* | Xylaria (lab) | Ustulina (lab) | Ustulina (zonal) |
| *F. pinicola* | 39.2 ± 6.1 | 5.7 ± 1.0 | 4.2 ± 1.5 | 5.0 ± 1.4 | 4.9 ± 1.0 |
| No fungus | 4.3 ± 1.1 | — | — | — | — |

TABLE 4B-2

Inhibition of Decay by Melanin-Borate Complex

| | No Treatment | Melanin Source | | | |
|---|---|---|---|---|---|
| | | *P. catenatus* | Xylaria (lab) | Ustulina (lab) | Ustulina (zonal) |
| *F. pinicola* | 39.2 ± 6.1 | 6.1 ± 1.1 | 5.9 ± 2.1 | 4.8 ± 0.1 | 6.5 ± 1.7 |
| No fungus | 4.3 ± 1.1 | — | — | — | — |

TABLE 4B-3

Inhibition of Decay by Melanin-Copper Complex

| | No Treatment | Melanin Source | | | |
|---|---|---|---|---|---|
| | | *P. catenatus* | Xylaria (lab) | Ustulina (lab) | Ustulina (zonal) |
| *F. pinicola* | 39.2 ± 6.1 | 6.3 ± 1.0 | 3.4 ± 0.8 | 3.8 ± 0.9 | 5.6 ± 1.1 |
| No fungus | 4.3 ± 1.1 | | | | |

(C) Metal ion analysis of samples of metal-complexed melanin solids prepared in (A)–(C) above was performed by Induced Coupled Plasma Emission Spectroscopy.

TABLE 4C-1

Copper Concentration in Various Copper-Melanin Complexes.

| Sample | $Cu^{2+}$ (ppm w/v) |
|---|---|
| $CuSO_4$ Stock solutions: | |
| X) 5 mM | 387.11 |
| Y) 10 mM | 647.8 |
| Z) 50 mM | 3,277.28 |

| Melanin Source: | mg/kg (ppm w/w)* |
|---|---|
| *P. catenatus* (control) | 9.72 |
| copper complexed[1] (Stock Sol. Y) | 44,556.39 |
| copper complexed[2] (Stock Sol. Z) | 122,875.90 |
| Xylaria (control) | 6.21 |
| copper complexed[2] (Stock Sol. X) | 37,798.03 |
| Ustulina (control) | 8.66 |
| copper complexed[2] (Stock Sol. X) | 46,751.53 |
| Ustulina zonal barrier[2] (control) | 2.97 |
| copper complexed (Stock Sol. X) | 35,978.15 |
| Wool Melanin (control) | 29.66 |
| copper complexed[1] (Stock Sol. Z) | 125,541.10 |

*mg of copper (expressed as the element) per kg of melanin
[1] from Example 4(A)
[2] from Example 4(B)

TABLE 4C-2

Boron Concentration in Various Borate-Melanin Complexes

| SAMPLE | Boron (ppm w/v) |
|---|---|
| 10 MM borate, pH 7.0 stock | 1,156.27 |

| | mg/kg (ppm w/w)* |
|---|---|
| *P. catenatus* melanin (control) | 14.99 |
| borate complexed | 1,146.71 |
| Xylaria melanin (control) | 31.22 |
| borate complexed | 2,709.53 |
| Ustulina melanin (control) | 45.17 |
| borate complexed | 3,848.67 |
| Zonal barrier melanin (control) | 8.56 |
| borate complexed | 5,496.08 |

*mg of boron (expressed as the element) per kg of melanin

TABLE 4C-3

Zinc Concentration in Zinc-Melanin Complexes.

| SAMPLE | Zinc (ppm w/v) |
|---|---|
| 50 mM $ZnSO_4$ stock solution | 3908.48 |

| | mg/kg (ppm w/w)* |
|---|---|
| P. catenatus melanin (control) | 156.60 |
| zinc complex | 31027.00 |
| Wool melanin (control) | 253.17 |
| Zinc complexed | 49003.39 |

*mg of zinc (expressed as the element) per kg of melanin

The above examples indicate that melanin compositions can be employed as fungicidal compounds, and that fungicidal activity can be improved by complexing the melanin with a metal ions such as copper, boron, or zinc.

EXAMPLE 5

Wound Dressing Preparation

In mid-August five aspen trees of the species, *Populus tremuloides*, in the Fon du lac State Forest in Cromwell, Minn. were wounded and various treatments applied. Each tree received 4 wounds made on the north, west, south and east side of the tree separated by approximately 30 cm. The top wound was located at approximately 2 meters above the ground. Wounds were made by drilling a hole 2.5 cm into the xylem with a ¼ inch drill bit. After the hole was made, a cork borer (0.6 inch dia.) was used to remove a circular region of bark and phloem around the drill hole.

Four wound dressings were prepared, as follows:

(a) Formulation "A" comprising 5 ml. 1 M NaOH to which 1 M HCl was added to lower pH to 5.5 (a buffer control);

(b) Formulation "B" comprising Ustulina zonal barrier melanin prepared by dissolving 1.0 g melanin in 5 ml. NaOH at 60° C. overnight, then adjusting pH to 5.5 with 1 M HCl;

(c) Formulation "C", a mixed suspension prepared by adding Formulation A to 2.5 ml. of lanolin which was warmed in a water bath, followed by mixing until uniform with a stirring rod.

(d) Formulation "D", a mixed suspension prepared by adding Formulation B to 2.5 ml. of lanolin which was warmed in a water bath, followed by mixing until uniform.

Each formulation was applied to each of the trees at the surface of a wound site. Treatment positions varied among the trees.

Approximately 0.8 ml of Formulations (A) and (B) were used. Treatments (C) and (D) were applied by warming the lanolin in a water bath and applying it to the wound with a spatula.

The trees were harvested the following year in mid-September.

A) The extent of wound closure was measured before the wounds were split for isolations. A percent of total wound closure was determined for each wound, as indicated on Table 5A. (100% wound closure signifies that the wound is completely closed with callus tissue.)

TABLE 5A

External wound-closure of treated wounds.*

| Tree # | "Buffer" control | Melanin alone | Lanolin alone | Lanolin + Melanin |
|---|---|---|---|---|
| 1 | 0 | 0 | 40 | 50 |
| 2 | 40 | 100 | 100 | 100 |
| 3 | 40 | 50 | 100 | 100 |
| 4 | 50 | 100 | 100 | 100 |
| 5 | — | — | — | — |

*% of wound that is closed. 100% equals a completely closed wound.
— Not determined due to loss of bark at a wound site during felling of the tree B) The area of discolored wood was also estimated by measuring one side (length×width) of the split wound. The area of discoloration is indicated on Table 5B.

TABLE 5B

Discoloration from xylem around wound.*

| Tree # | "Buffer" control | Melanin alone | Lanolin alone | Lanolin + Melanin |
|---|---|---|---|---|
| 1 | 63 | 70 | 70 | 35 |
| 2 | 56 | 65 | 94 | 42 |
| 3 | 270 | 165 | 465 | 77 |
| 4 | 91 | 216 | 128 | 60 |
| 5 | 144 | 72 | 102 | 91 |
| Total | 624 | 588 | 849 | 305 |

*Discoloration determined length and width of discolored column from exposed surface of one of the bolts and determining length × width.

C) 50 chip samples were removed from each wound site. Isolations for each chip were made aseptically on a semi-select media for isolating basidiomycetes (consisting of 15 g. Difco Malt Extract, 15 g. Difco Agar, 60 ppm Benlate, 30 ppm streptomycin sulfate and 4 cc. of 85% lactic acid.) The percent of chips from around the wound containing basidiomycetes is indicated on Table 5C.

TABLE 5C

Isolations for Basidiomycetes from wood around wound.

| Tree # | "Buffer" control | Melanin alone | Lanolin alone | Lanolin + Melanin |
|---|---|---|---|---|
| 1 | 9 | 8 | 0 | 0 |
| 2 | 10 | 0 | 10 | 6 |
| 3 | 6 | 0 | 0 | 0 |
| 4 | 10 | 1 | 0 | 0 |
| 5 | 5 | 10 | 0 | 0 |
| Total | 40 | 19 | 10 | 6 |
| % of 50 chips isolated | 80% | 38% | 20% | 12% |

The above example demonstrates that melanin compositions can provide effective wound dressing compositions, and can be effectively combined with lanolin.

EXAMPLE 6

Application of melanin precursor to tree wounds

A. D,L-DOPA

Five grams of D,L-DOPA were dispersed in 500 ml. of de-ionized water in a brown bottle to form a clear aqueous medium. A day later, this medium was sprayed onto a round ¾ in.×1 in. deep wound of an aspen tree, *Populus tremuloides*, and allowed to soak in for approximately 20–30 minutes. The wound was then sprayed with 1 M Tris buffer, pH 9.0.

Within 30 minutes of application of the DL-DOPA, the treated tree wound started to turn black in color.

B. Catechol 20 grams of catechol were dissolved in 500 ml. of de-ionized water and stored in a brown bottle until use. The catechol solution were applied to a wound of *Populus tremuloides*, following the above procedure. The wound surface was also observed to turn black in color within five minutes after treatment.

EXAMPLE 7

Melanin Precursor Field Study

Aspen trees, *Populus tremuloides*, approximately 8 to 10 inch diameter at breast height, received 6 wounds made 12" apart, spiraling around the tree. Each wound was 0.75 inch diameter and 1.0 inch deep. To each wound was applied a fine spray comprising one of the following:

1. 3 ml. solution of D,L-DOPA (5 g/500 ml), followed by a 1 ml. distilled water;

2. 3 ml. solution of D,L-DOPA (5 g/500 ml); followed by a 1 ml. of 1 M Tris buffer (adjusted to pH 9.0);

3. 3 ml. solution of catechol (20 g/500 ml) followed by 1 ml. of 1 M Tris buffer (pH 9.0);

4. 3 ml. solution of D,L-DOPA (2.5 g/500 ml) followed by 1 ml. of 1 M Tris buffer (pH 9.0);

5. control, 1 M Tris buffer solution (pH 9.0); and 6. control, distilled water spray only.

Evaluation after six months shows satisfactory protection of the wounds to which the melanin precursor compositions, 1–4, have been applied.

What is claimed is:

1. The method of preserving a plant substrate subject to decay by microbial or environmental factors comprising applying to at least a surface of the substrate a decay-inhibiting effective amount of a preservative composition comprising melanin, a melanin precursor or a mixture thereof, and causing any such melanin precursor in said composition to polymerize to form melanin, such melanin being optionally in metal complexed form.

2. The method of claim 1 in which the substrate comprises cellulose.

3. The method of claim 2 in which the substrate is of harvested plant material.

4. The method of claim 2 in which the preservative composition comprises melanin complexed with metal ions.

5. The method of claim 3 in which the composition comprises melanin complexed with ions of at least one metal.

6. The method of claim 5 in which the metal is boron, selected from the group consisting of copper, manganese, boron, tin, aluminum, zinc, nickel, cobalt, cadmium, calcium, magnesium, sodium and mixtures thereof.

7. The method of claim 3 in which the melanin is obtained from wool.

8. The method of claim 3 in which the melanin is obtained from a fungus.

9. The method of claim 8 in which the fungus is from a genus selected from the group consisting of Ustulina, Xylaria, Hypoxylon, Ganoderma, Armillaria, Ophiostoma, and Aureobasidium and Phaeococcomyces.

10. An article of manufacture comprising a plant substrate having at least one surface portion thereof susceptible to decay by microbial or environmental factors, at least said surface portion having applied thereto a decay-inhibiting effective amount of a preservative composition comprising melanin, melanin reactively bound with an anti-microbial agent, or a mixture thereof.

11. An article in accord with claim 10 in which at least said surface portion is of tree wood.

12. An article in accord with claim 10 in which said substrate is a plant seed.

13. An article in accord with claim 10 in which said composition comprises melanin complexed with metal ions.

14. An article in accord with claim 10 in which the melanin is obtained from wool.

15. An article in accord with claim 14 in which the melanin is obtained from wool of the genus Ovis.

16. The method of claim 2 in which the substrate surface to which the composition is applied in a plant wound.

17. The method of claim 16 in which the melanin is obtained from wool.

18. The method of claim 16 in which the composition comprises melanin complexed with metal ions.

19. The method of claim 1 wherein the melanin precursor is selected from D,L-DOPA, D-DOPA, L-DOPA, tyrosine, 5,6-dihydroxyindole, catechol, 1,8-dihydroxynaphthalene, 5,6-dihydroxyindole-2-carboxylic acid, tyramine, 3-hydroxytyramine, tyrosine, 5-hydroxyindole, leucodopachrome, tryptamine, serotonin, epinephrine, norepinephrine, adenochromedopamine, m-aminophenol, o-aminophenol, p-aminophenol, 4-aminocatechol, 4-methylcatechol, 2-hydroxy-1,4-naphthaquinone, 3,4-dihydroxybenzylamine, 3,4-dihydroxybenzoic acid, 1,2-dihydroxynaphthalene, gallic acid, resorcinol, 4,5-dihydroxynaphthalene-2,7-disulfonic acid, p-aminophenol, and mixtures thereof.

20. The method of claim 19 wherein the melanin precursor is selected from D,L-DOPA, L-DOPA, and catechol.

21. The method of claim 20 wherein the melanin precursor is catechol.

22. The method of claim 2 in which the substrate is of living plant material.

23. The method of claim 22 in which the composition comprises melanin in metal complexed form, wherein the metal is selected from the group consisting of copper, boron, zinc, tin, aluminum, and mixtures thereof.

24. The method of claim 6 in which the metal is selected from the group consisting of copper, boron, zinc, tin, aluminum, and mixtures thereof.

25. The method of claim 24 in which the metal is copper.

26. The method of claim 1 in which the melanin is DOPA melanin.

27. The method of claim 19 wherein the precursor is 1,8-dihydroxynaphthalene.

28. The method of claim 16 in which the composition additionally comprises lanolin.

29. An article in accord with claim 13 in which the metal is selected from the group consisting of copper, boron, zinc, tin, aluminum, and mixtures thereof.

30. An article in accord with claim 29 in which the metal is copper.

31. An article in accord with claim 10 in which the melanin is DOPA melanin.

32. An article in accord with claim 10 in which the melanin is derived from a precursor selected from DOPA, catechol and 1,8-dihydroxynaphthalene.

33. An article in accord with claim 11 in which the composition additionally comprises lanolin.

* * * * *